US007066957B2

(12) United States Patent
Graf (10) Patent No.: US 7,066,957 B2
(45) Date of Patent: Jun. 27, 2006

(54) DEVICE AND ASSEMBLY FOR INTERVERTEBRAL STABILIZATION

(75) Inventor: Henry Graf, Lyons (FR)

(73) Assignee: SDGI Holdings, Inc., Wilmington, DE (US)

( * ) Notice: Subject to any disclaimer, the term of this patent is extended or adjusted under 35 U.S.C. 154(b) by 0 days.

(21) Appl. No.: 10/168,679

(22) PCT Filed: Dec. 28, 2000

(86) PCT No.: PCT/FR00/03727

§ 371 (c)(1),
(2), (4) Date: Jun. 26, 2002

(87) PCT Pub. No.: WO01/49192

PCT Pub. Date: Jul. 12, 2001

(65) Prior Publication Data

US 2003/0009226 A1   Jan. 9, 2003

(30) Foreign Application Priority Data

Dec. 29, 1999  (FR)  .................................. 99 16662

(51) Int. Cl.
    *A61F 2/44* (2006.01)
(52) U.S. Cl. .................................. 623/17.12
(58) Field of Classification Search ............ 623/11.11,
        623/16.11, 17.11, 17.12; 606/60, 61; 267/33–35,
        267/136, 140, 152, 153, 64.16–64.17; 188/379–380,
                                       188/316, 317, 319.1, 318
See application file for complete search history.

(56) References Cited

U.S. PATENT DOCUMENTS

| | | | |
|---|---|---|---|
| 3,316,558 A * | 5/1967 | Mortensen .................... 623/26 |
| 3,648,294 A | 3/1972 | Shahrestani |
| 3,853,311 A * | 12/1974 | Kreuzer et al. .......... 267/64.26 |
| 4,066,279 A * | 1/1978 | Kaptanis ................... 267/64.11 |
| 4,458,888 A * | 7/1984 | Wolf et al. ............ 267/140.12 |
| 4,504,044 A * | 3/1985 | Shtarkman ................... 267/35 |
| 4,509,730 A * | 4/1985 | Shtarkman ................... 267/35 |
| 4,830,346 A * | 5/1989 | Eberhard et al. ...... 267/140.13 |
| 4,932,969 A * | 6/1990 | Frey et al. ............... 623/17.12 |
| 5,295,563 A * | 3/1994 | Bennett ................... 188/266.2 |
| 5,375,823 A * | 12/1994 | Navas ...................... 623/17.15 |
| 5,376,138 A * | 12/1994 | Bouchard et al. ............. 623/44 |
| 5,460,355 A * | 10/1995 | Danek ........................ 267/221 |
| 5,466,261 A * | 11/1995 | Richelsoph .............. 623/23.47 |

(Continued)

FOREIGN PATENT DOCUMENTS

EP          0277282          8/1988

(Continued)

*Primary Examiner*—Eduardo C. Robert
*Assistant Examiner*—Anuradha Ramana
(74) *Attorney, Agent, or Firm*—Kreig DeVault LLP (57) ABSTRACT

The invention concerns a staiblizing device (150) designed to link two vertebrae, comprising at least two chambers (156, 158, 186, 188) arranged proximate to said vertebrae, said chambers containing a shock absorbing fluid. Means (192, 194) are provided for providing fluid communication with controlled flow between said two chambers, thereby adequately damping the patient's movements.

5 Claims, 6 Drawing Sheets

U.S. PATENT DOCUMENTS

| | | | |
|---|---|---|---|
| 5,540,688 A * | 7/1996 | Navas | 606/61 |
| 5,562,737 A * | 10/1996 | Graf | 623/17.14 |
| 5,775,677 A * | 7/1998 | Englund | 267/64.11 |
| 5,961,516 A * | 10/1999 | Graf | 606/61 |
| 6,082,508 A * | 7/2000 | Davis | 188/298 |
| 6,322,059 B1 * | 11/2001 | Kelm et al. | 267/119 |
| 6,692,495 B1 * | 2/2004 | Zacouto | 606/61 |
| 6,835,207 B1 * | 12/2004 | Zacouto et al. | 623/17.12 |
| 2002/0151978 A1 * | 10/2002 | Zacouto et al. | 623/17.12 |

FOREIGN PATENT DOCUMENTS

| | | |
|---|---|---|
| EP | 0820731 | 1/1998 |
| EP | 0953317 | 11/1999 |
| FR | 2723841 | 3/1996 |

* cited by examiner

DEVICE AND ASSEMBLY FOR INTERVERTEBRAL STABILIZATION

CROSS REFERENCE TO RELATED APPLICATIONS

The above referenced application is based on PCT Application PCT/FR00/03727, filed on Dec. 28, 2000, having the same inventor, which claims priority from French Patent Application No. 99/16662 which was filed on Dec. 29, 1999 also having the same inventor.

BACKGROUND OF THE INVENTION

The present invention relates to a device and an assembly for intervertebral stabilisation.

Such a device is usually intended to replace all or part of an intervertebral disc, when the latter has been destroyed by surgery or disease.

BRIEF SUMMARY OF THE INVENTION

The invention proposes to produce a stabilising device which ensures a relative movement between the two vertebrae that it connects, which is sufficiently close to the movement allowed by a natural vertebral disc for no major dysfunction to appear at the level of the whole of the vertebral chain.

To that end, it has for its object a device for intervertebral stabilisation, designed to link two vertebrae, characterized in that it comprises:

at least two chambers intended to be arranged in the proximity of said vertebrae, said chambers containing a fluid, and means for placing said chambers in fluid communication with controlled fluid flow.

The invention also has for its object an assembly for intervertebral stabilisation comprising at least two intervertebral stabilisation devices such as defined hereinabove, at least first and second devices being arranged on either side of the principal axis of the vertebral chain.

BRIEF DESCRIPTION OF THE SEVERAL VIEWS OF THE DRAWINGS

The invention will be described hereinafter with reference to the accompanying drawings, given solely by way of non-limiting examples and in which.

DETAILED DESCRIPTION OF THE INVENTION

Figure 1:
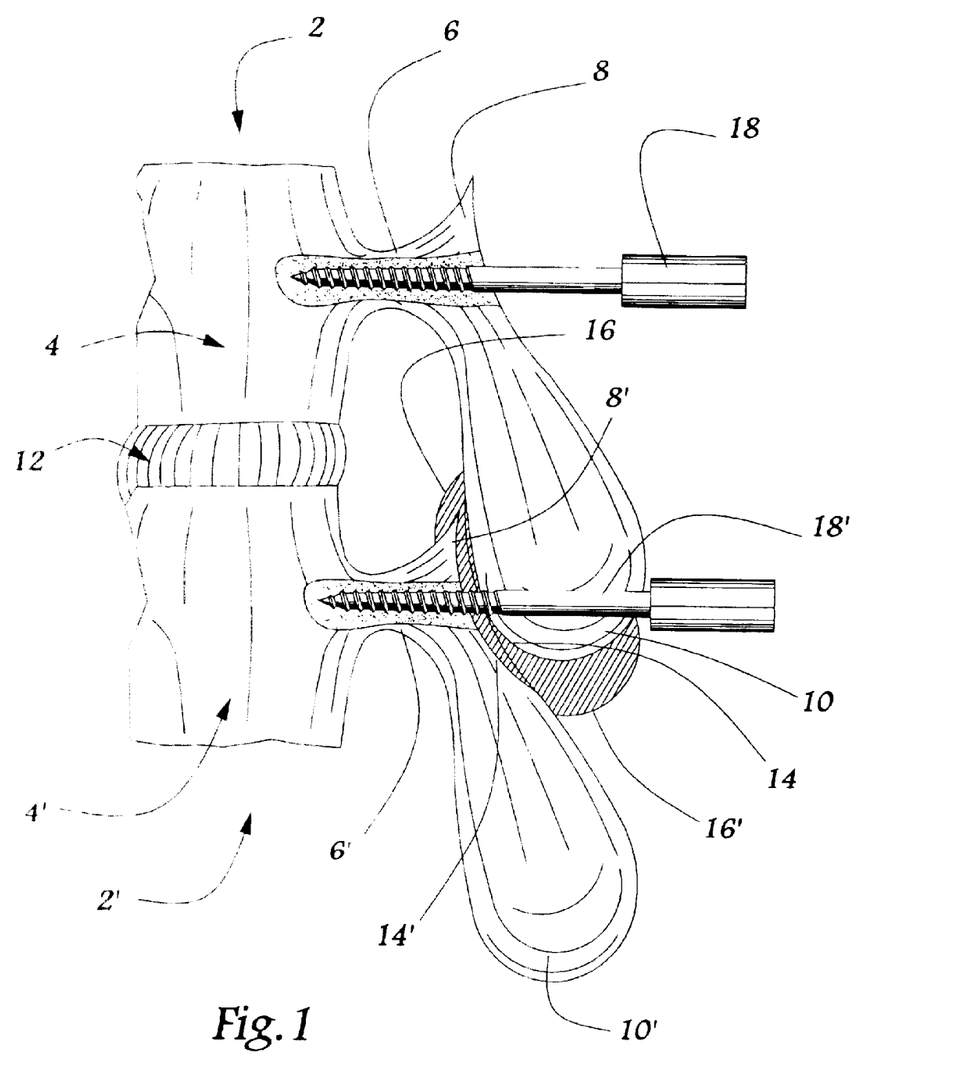
FIG. 1 is a schematic side view, illustrating two adjacent vertebrae between which different stabilising devices according to the invention are intended to be placed.

FIG. 1 shows two vertebrae, upper 2 and lower 2' respectively, intended to be linked via different types of stabilising devices according to the invention, which will be described in the following. Each vertebra comprises a vertebral body 4, 4' extended by a pedicle 6, 6', an upper articular process 8, 8' and a lower articular process 10, 10', 12 denotes the intervertebral space, 14, 14' the opposite articular surfaces and 16 and 16' the articular capsules.

This FIG. 1 also shows two pedicular screws 18, 18' fixed in the corresponding vertebral bodies 4, 4'.

Figure 2:
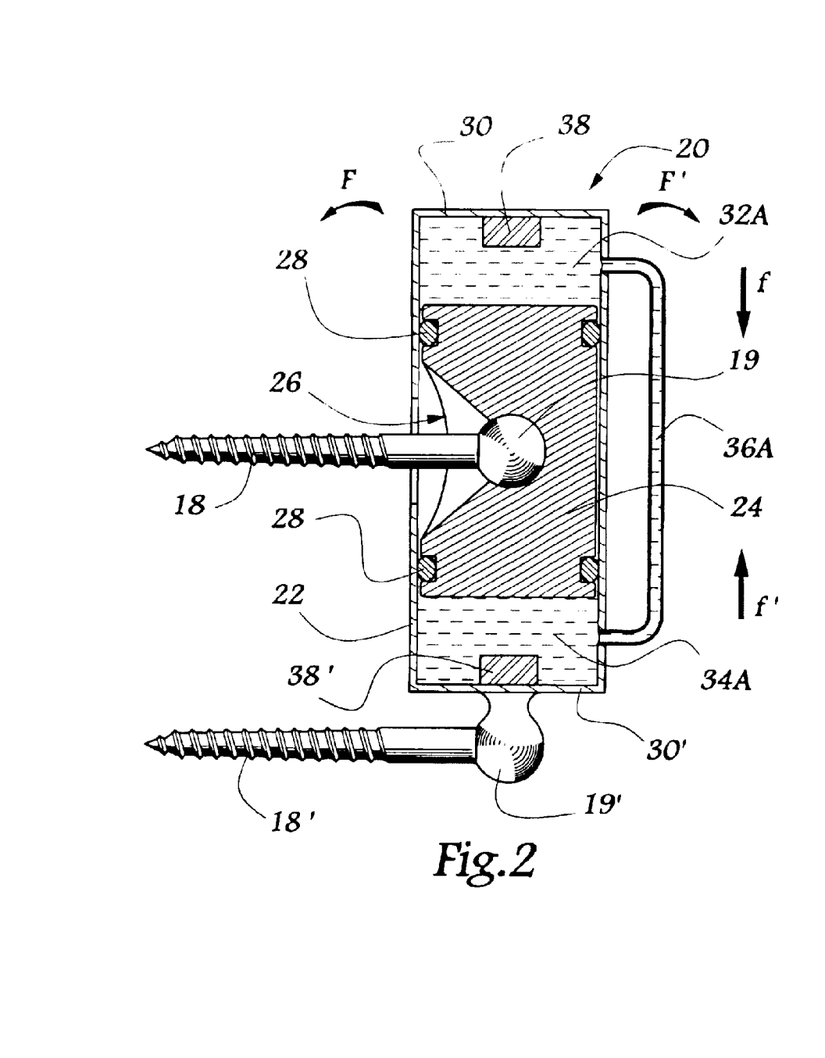
FIG. 2 is a side view, on a larger scale, illustrating a first embodiment of a stabilising device according to the invention.

FIG. 2 shows a device for intervertebral stabilisation according to a first embodiment of the invention, which forms an extra-discal member 20. This latter, which is disposed to the rear of the intervertebral space 12, is capable of damping a displacement between the vertebrae 2, 2'.

The damping member 20 comprises a rigid cylindrical vessel 22, made for example of metal, plastics material, or ceramics. This vessel receives, in its internal volume, a piston 24 which is mounted to pivot on the head 19 of the screw, which screw extends through an opening 26 made in the vessel 22. The lateral walls of the piston are separated from the opposite inner walls of the vessel via two O-rings 28. Furthermore, the lower end of the vessel 22 is connected to the head 19' of the lower screw 18'.

The end walls 30 of the vessel 22 define, with the opposite end walls of the piston 24, two respectively upper (32A) and lower (34A) chambers. These latter are placed in communication by a conduit 36A, extending in the principal direction of the vessel 22. This conduit, which is for example made of metal or plastics material, is connected to the vessel 22 by crimping, screwing or clipping. The cross-section of this conduit 36A is substantially smaller than the cross-section of each chamber 32A, 34A. This conduit 26A presents, for example, a diameter for passage less than 2 mm, advantageously included between 0.2 and 0.9 mm.

The end walls 30 of the vessel 22 are in addition provided with stops 38, made of a supple material such as a polymer. Each chamber is filled with a damping fluid. This fluid comprises at least one liquid, such as water or oil.

Functioning of this damping member 20 is as follows: When the patient leans forward in the direction of arrow F, this has the effect of moving the vertebrae 2, 2' and therefore the pedicular screws 18, 18' away from one another. Consequently, the mobile piston 24, for separating the chambers, is directed towards the upper wall 30 of the vessel 22 and thus drives the fluid out of the upper chamber 32A, in the direction of the lower chamber 34A. This flow, which is produced through conduit 36A, is materialized by arrow f.

It will be appreciated that the speed of displacement of the fluid through the conduit 36A, which determines the speed of displacement of the piston 24 in the direction of the upper wall 30' is adjustable as a function of the section of the conduit, of the length of the latter and of the viscosity of the fluid employed. The presence of this fluid which must be driven out of the chamber in question in order to allow a given movement of the patient, gives a satisfactory component of damping to this movement.

During a movement of great amplitude of the patient, the upper stop 38 makes it possible to limit the afore-mentioned movement, by abutment of the opposite wall of the piston 24 against this stop 38. The elastic nature of the latter gives an additional component of damping. In a variant, it may be provided that at least one chamber contains a hydrophilic body, such as hydrogel. As the piston continues its stroke, the latter abuts on the hydrophilic body so as progressively to release the fluid which was contained therein.

Inversely, when the patient leans backwards in the direction of arrow F', the piston 24 is directed towards the lower wall 30' of the vessel 22, with the result that the fluid is driven from this chamber 34A through the conduit 36A, in the direction of arrow f'.

Figure 3:
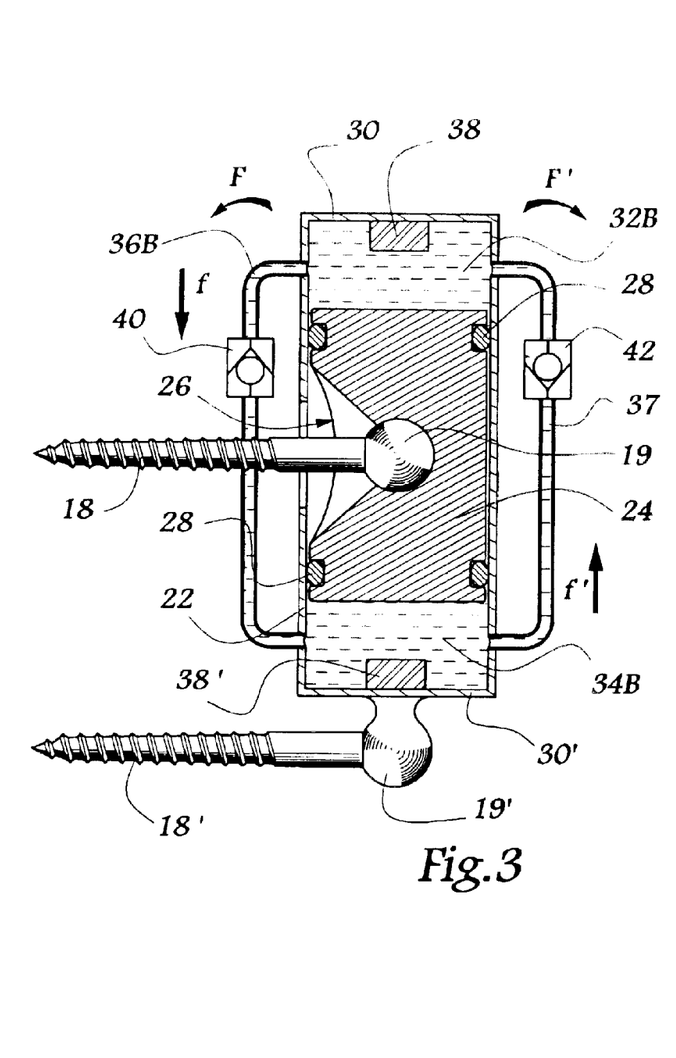
FIG. 3 is a view similar to FIG. 2, illustrating a variant of the stabilising device described in this FIG. 2.

FIG. 3 shows a variant embodiment of the damping member 20 described in FIG. 2.

In this embodiment, it employs an additional conduit 36B linking the two chambers 32B, 34B. Moreover, each conduit 36B, 37 is provided with a corresponding non-return valve 40, 42. Consequently, the conduit 36B allows only a transfer of fluid from the upper chamber 32B towards the lower chamber 34B, in the direction of arrow f, while conduit 37 ensures a movement of the fluid only from the lower chamber 34B towards the upper chamber 32B, in the direction of arrow f'.

The transverse dimensions of the conduit 36B for passage, ensuring the flow towards the lower chamber, are advantageously larger than those of the conduit 37 ensuring passage towards the upper chamber 32. This makes it possible to give a greater component of damping in the direction of intervertebral extension. In other words, the movements of forward bending of the patient are damped to a lesser extent than those of rearward extension.

Figure 4:
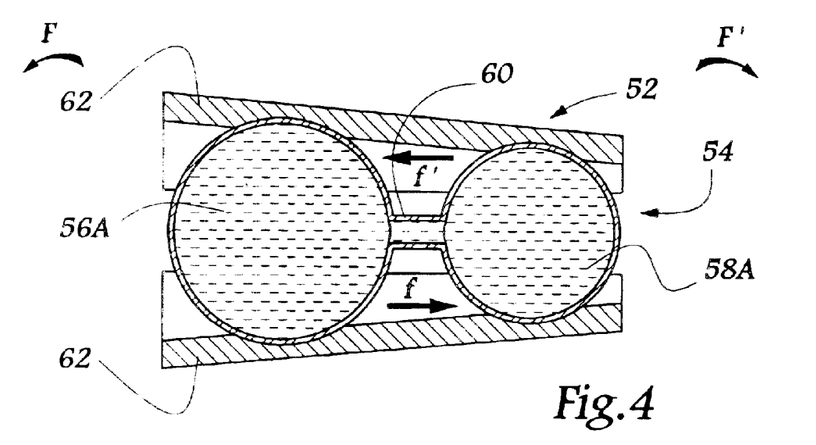
FIG. 4 is a schematic side view, illustrating a second embodiment of a stabilising device according to the invention.

FIG. 4 illustrates a device for intervertebral stabilisation in accordance with a second embodiment, which forms a discal implant 52 intended to be inserted at least partially between the vertebral bodies 4, 4' of the vertebrae 2, 2' of FIG. 1.

This implant comprises a bag 54, made of a deformable but substantially non-extensible material. This bag 54 defines two respectively front (56A) and rear (58A) chambers which are joined by a conduit 60A, or constriction, placing the internal volume of these two chambers in communication. This conduit 60 presents transverse dimensions substantially smaller than those of chambers 56A, 58A.

The implant 52 also comprises a coating formed by two shells 62. Each of the latter, which presents a cross-section substantially in the form of an arc of circle, is made of a rigid material, such as titanium. These shells 62, which are placed on either side of a median plane of the bag 54, are intended to come into contact with the vertebral bodies 4, 4'. They are fastened to the bag 54 for example by gluing.

Each chamber 56A, 58A is filled with a fluid, similar to that contained in the aforementioned chambers 32, 34. Once the implant 52 is in position, when the patient leans forwards in the direction of arrow F, this has the effect of compressing the front chamber 56A and therefore of driving the fluid which was initially contained therein, in the direction of the rear chamber 58A. This flow of fluid, which is effected through conduit 60, is materialized by arrow f.

Inversely, when the patient leans backwards in the direction of arrow F', there is produced, by a similar phenomenon, a flow of fluid along conduit 60, materialized by arrow f'. The intensity of the damping thus given during the movements of bending and of extension of the patient, depends on the section of passage and on the length of the conduit 60, as well as on the physico-chemical characteristics, in particular the viscosity, of the fluid admitted in chambers 56A, 58A.

Figure 5:
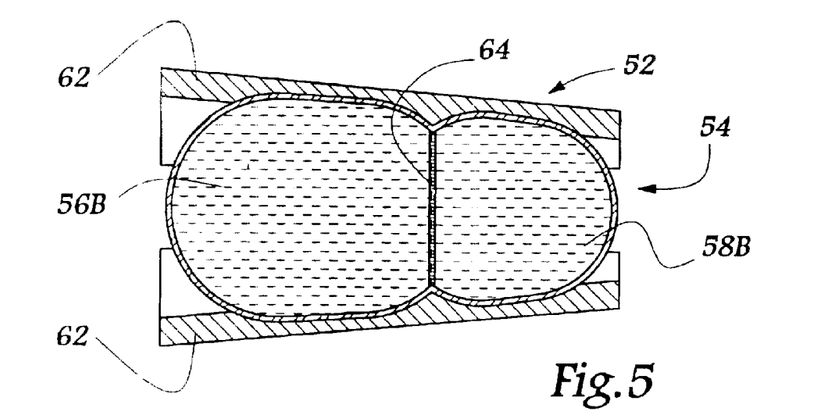
FIGS. 5 to 8 are views similar to FIG. 4, illustrating variants of the stabilising device described in this FIG. 4.

FIG. 5 shows a variant embodiment of the implant 52 of FIG. 4. In this variant, the two chambers 56B, 58B are joined, not by a conduit, but by a porous membrane 64, constituting an interface between these two chambers. This membrane 64, which may extend over the whole transverse section of the chambers 56B. 58B, is for example made of a textile material, such as DACRON, or of a porous metal. The presence of the pores of this membrane 64 makes it possible to delay, in manner similar to the use of the conduit 60, the transfer of fluid between the two chambers. The component of damping thus conferred depends in particular on the size and the number of the pores of the membrane 64.

Figure 6:
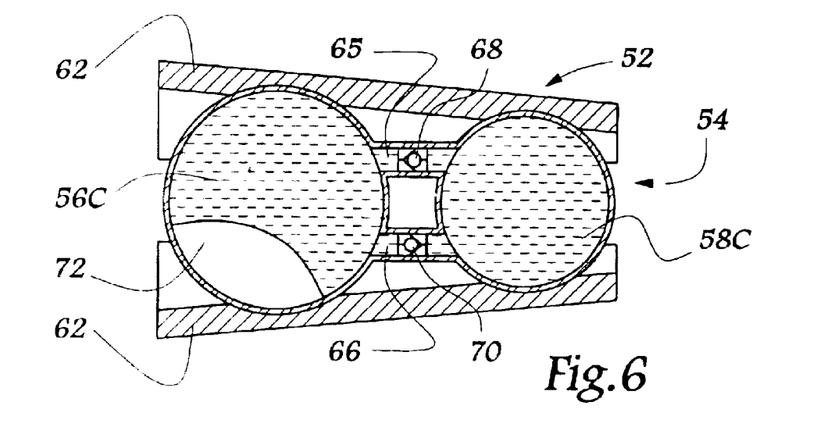

FIG. 6 shows an additional variant embodiment of the implant 52 described in FIG. 4. In this FIG. 6, the chambers 56C, 58C are connected, not only by a first conduit 65, but also by an additional conduit 66, parallel to conduit 65. Each conduit is provided with a respective non-return valve 68, 70. Consequently, the conduit 65 allows a transfer of fluid solely from the front chamber 56C towards the rear chamber 58C, while the additional conduit 66 ensures a transfer of fluid solely in the opposite direction.

The transverse dimensions of the conduit 65 are advantageously larger than those of the additional conduit 66, with the result that the fluid is more easily able to flow in the direction of the rear chamber 58C, which corresponds to the movement of forward bending of the patient. In other words, this forward bending movement is damped to a lesser degree than the inverse movement of rearward extension.

As shown in this FIG. 6, at least one of the chambers belonging to the implant, in the present case the front chamber 56C, contains a volume of gas 72 which may for example be air or nitrogen.

The presence of this gas 72 is advantageous insofar as it induces an elastic effect during compression of the chamber 56C. In effect, when the latter is compressed, it is firstly the air 72 which is driven therefrom, with the result that the corresponding movement is damped only to a very small degree.

Once the air is driven out, it is then the fluid initially contained in the chamber which flows in conduit 65, which gives a much greater damping component. Consequently, during movements of low amplitudes, only air flows through the conduit 65, with the result that these movements are only slightly damped. This is not detrimental as, due to their low amplitude, such movements cannot harm the physical integrity of the patient. On the other hand, when the aforementioned movements have a higher amplitude, fluid also flows through the conduit 65, with the result that such movements are damped to a greater degree.

Figure 7:
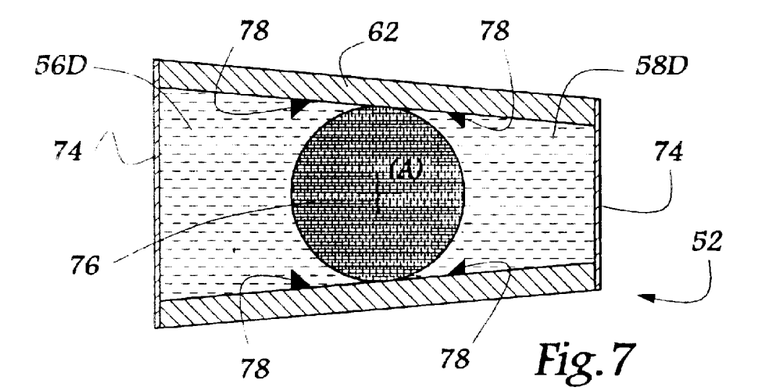

FIG. 7 shows an additional variant of the implant 52. In this variant, the implant 52 has no bag 52, but presents end walls 74 hermetically joining the shells 62. These walls 74 are made of a deformable but substantially non-extensible material. Furthermore, a frustum of cylinder 76, forming piston, is housed in the internal volume of the implant 52. This frustum of cylinder, of which the principal axis is transverse with respect to that of the implant 52, forms a porous system. For example, it contains a labyrinth system comprising small cells linked together by pores, which allows it to capture the fluid so as to provoke a slowing down of the flow of the latter.

The movement of the piston from rear to front of the implant 52 is limited, in two opposite directions, by stop means 78. This piston 76 defines, with the opposite walls 74, two front (56D) and rear (58D) chambers.

During movements of flexion or of extension of the patient, the mobile piston 76, for separating the chambers, moves from rear to front of the implant 52. This induces a compression of one of the chambers 56D, 58D, with the result that fluid escapes therefrom in the direction of the other chamber, via the pores of the piston 76.

Figure 8:
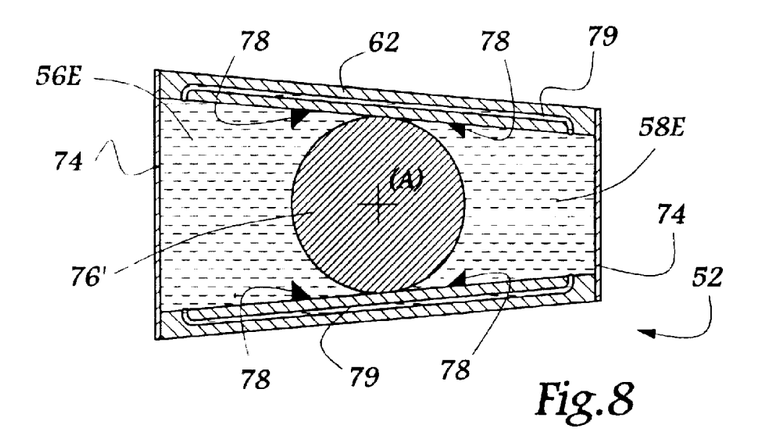

FIG. 8 shows a variant embodiment of FIG. 7, in which the piston 76' is rigid and tight. This piston constitutes, as in the embodiment of FIG. 7, a pivot for the two shells 62, which may pivot with respect to each other about the transverse principal axis A of this pivot. The circulation of fluid between chambers 56E and 58E, which is not allowed by the piston 76', is ensured via at least one channel 78 made in one of the rigid shells 62.

Figure 9:
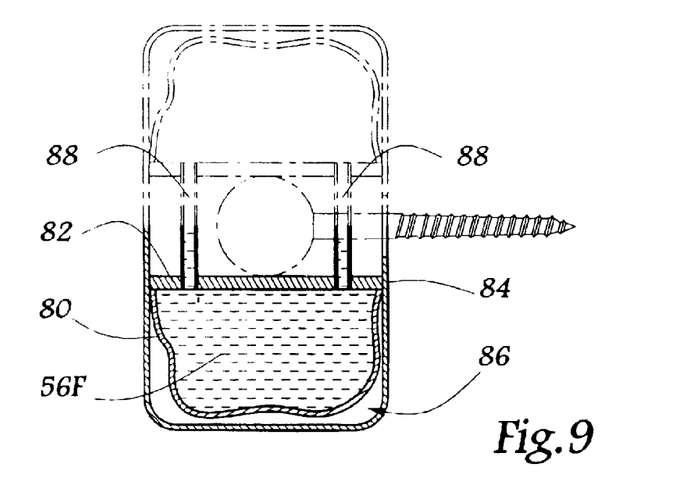
FIG. 9 illustrates a variant embodiment of a chamber belonging to a stabilising device according to the invention.

FIG. 9 illustrates an additional variant of the invention. It shows a chamber 56F, capable of being used in one of the implants described with reference to the preceding Figures. This chamber 56F comprises a bag 80, deformable but non-extensible, of which the open end is fixed, for example by crimping, to a rigid cover 82, which is mounted to slide in a vessel 84 with closed bottom. The opposite walls of the bag 80 and of the vessel 84 are separated by a lubricant 86, such as a silicone gel.

A conduit 88 traverses the cover 82, so as to place the internal volume of the chamber 56F in communication with the outside. As a function of the pressure conditions exerted on the chamber 56F, fluid escapes therefrom or is admitted therein, with the result that the edges of the cover 82 rise or descend, slidably, along the lateral walls of the vessel 84. This embodiment is advantageous, insofar as it guarantees a very satisfactory tightness, being given that such tightness is ensured both by the deformable walls of the bag and by the rigid walls of the vessel 84.

As shown in dotted lines in FIG. 9, two chambers 56F may be joined by the conduits 88, so as to form an extra-discal member, of the same type as that, 20, of FIGS. 2 and 3. These chambers 56F may also be surrounded by shells, similar to those, 62. In that case, the conduits 88 extend in the shells and at least one chamber may be surrounded by a helical spring.

Figure 10:
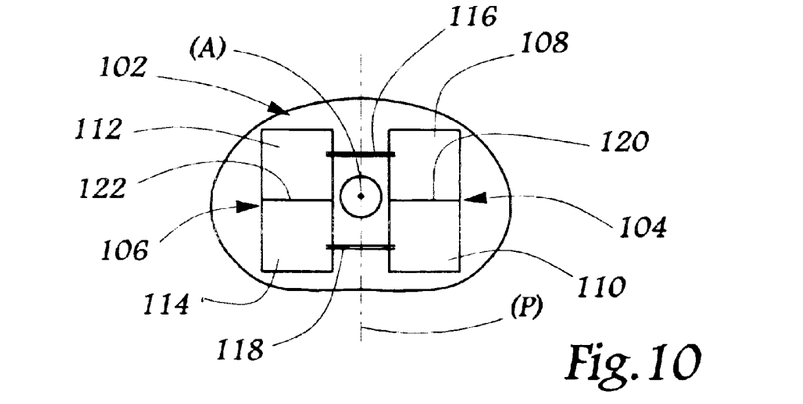
FIGS. 10 and 11 are plan views illustrating two stabilising devices in accordance with a third embodiment of the invention.

FIG. 10 illustrates a device for intervertebral stabilisation in accordance with another embodiment, which forms a discal implant 102. The latter comprises two respectively left (104) and right (106) elements, disposed on either side of the principal axis A of the vertebral chain which, when the patient is in standing position, is a vertical axis passing through the median plane P extending from rear to the front of the patient.

Each element 104, 106 comprises two respectively front (108, 112) and rear (110, 114) chambers. The two front chambers 108, 112 are placed in communication by a front conduit 116, while the two rear chambers 110, 114 are connected by a rear conduit 118. The different chambers contain a fluid similar to one of those described hereinabove, with the result that, as a function of the pressure conditions exerted on these chambers, a fluid communication is established therebetween.

The chambers of the same element are separated by means of respective membranes 120, 122 which may be tight, or porous like the membrane 64 described hereinabove. Consequently, the two chambers 108, 110 and 112, 114 of an element in question may possibly be placed in fluid communication.

In a variant, the front right chamber 108 may be placed in fluid communication with the rear left chamber 114, the front left chamber 112 being in that case placed in fluid communication with the rear right chamber 110. These additional fluid relations may be made additionally to the relations allowed by conduits 116, 118.

Figure 11:
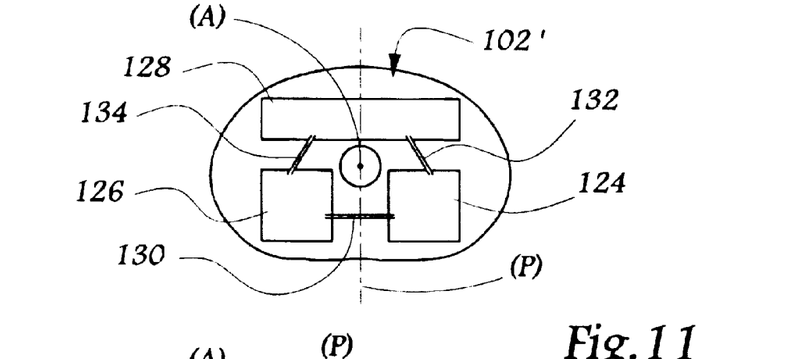

FIG. 11 shows a discal implant 102' comprising two respectively right (124) and left (126) rear chambers, as well as a front chamber 128, extending over a substantial part of the width of the disc. The rear chambers 124, 126 are placed in fluid communication via a conduit 130. Moreover, each of these chambers 124, 126 is placed in fluid communication with the front chamber 126, via respective conduits 132, 134.

The implants 102, 102', described hereinabove, induce an additional component of damping, when the patient leans towards the sides, being given that they employ chambers disposed on either side of the axis A.

Figure 12:
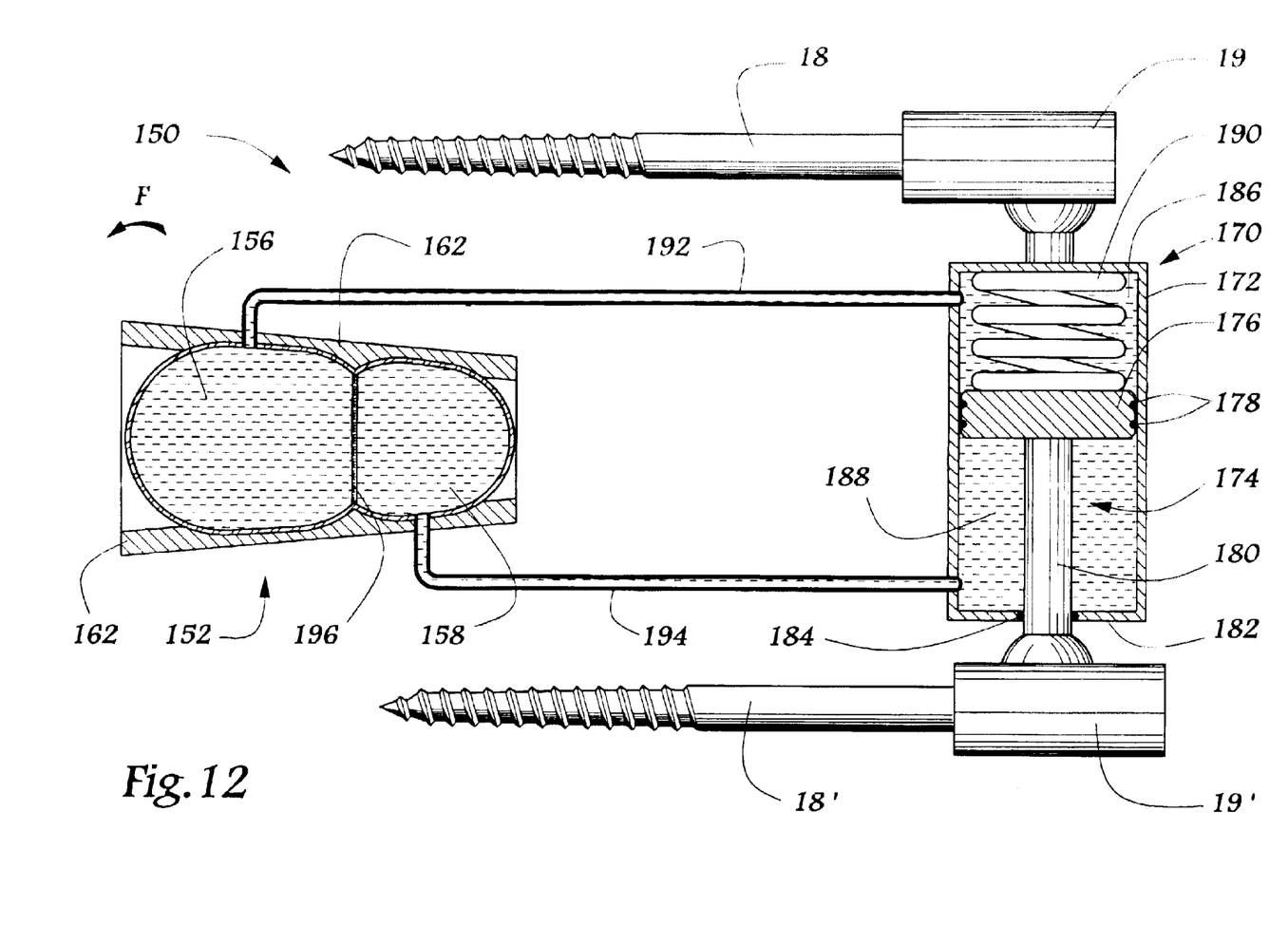
FIG. 12 is a side view illustrating a device for intervertebral stabilisation in accordance with a fourth embodiment of the invention.

FIG. 12 shows a device for intervertebral stabilisation in accordance with an additional embodiment, which is generally designated by reference 150. This device comprises a discal implant 152, intended to be inserted at least partially in the intervertebral space 12. This implant 152 comprises two respectively front (156) and rear (158) chambers, surrounded by two shells 162, similar to those, 62, described hereinabove.

The device 150 also comprises a damping member 170, arranged similarly to that, 20, described previously, namely to the rear of the intervertebral space 12. This member 170 comprises a rigid vessel 172 inside which is disposed a piston 174 which comprises a head 176, forming upper end, whose transverse dimensions are similar to those of the vessel. An O-ring 178 is mounted between the opposite walls of the head 176 and of the vessel 172.

The head 176 of the piston extends from a vertical rod 180 which traverses the lower wall 182 of the vessel 172 tightly, with the interposition of an O-ring 184. The lower end of the rod 180, opposite the head 176, is pivotally mounted on the head 19' of the lower screw 18'.

The head 176 defines respectively upper (186) and lower (188) chambers of the vessel 172. The upper chamber 186 receives a spring 190, working in compression, which extends vertically between the upper wall of the vessel and the opposite wall of the head 176. The use of this spring 190 allows the piston 174 to be returned into its low position, which corresponds to a physiologically advantageous lordosic posture of the patient.

The front chamber 156 of the implant 152 is placed in fluid communication with the upper chamber 186 of the member 170, via a conduit 192, while the rear chamber 158 is placed in fluid communication with the lower chamber 188 via an additional conduit 194. Consequently, when the patient leans forward in the direction of arrow F, fluid is driven from the front chamber 156 in the direction of the upper chamber 186, which contributes to causing the piston 174 to descend in the vessel 172, opposite the upper screw 18. This rise induces a displacement of fluid, through the conduit 194, from the lower chamber 188 towards the rear chamber 158. This movement of bending is therefore damped by these different flows of fluid The amplitude of such damping may be modulated as a function of the characteristics of the fluid admitted in the different chambers and of the section of passage of the conduits 192, 194. It will be readily appreciated that, during a movement of extension of the patient towards the rear, there are produced both flows of fluid and a movement of the piston 174, in directions opposite those mentioned above.

In a variant, it may be provided to add two additional conduits to each of the conduits 192, 194, the four conduits thus formed being provided with non-return valves ensuring the flow of the fluid in one direction only. It may also be provided that the membrane 196 separating the front (156) and rear (158) chambers be porous, so as to allow a flow of fluid between these two chambers. It may also be provided to eliminate this membrane 196, so as to form a single intradiscal chamber, placed in communciation with the lower chamber 174 by the conduit 192, the other conduit 194 in that case being eliminated. It may also be provided that the head 176 of the piston 174 be porous, like the one, 76, described hereinabove.

It may also be provided that the two upper (186) and lower (188) chambers be placed in fluid communication by a conduit, similar to that, 36, described hereinabove. These chambers 186, 188 may be placed in communication by a plurality of conduits extending in the wall of the vessel 172. These conduits may be disposed below one another, with the result that the head 176 of the piston, as it moves, successively obturates the openings of these conduits. At the end of movement, there therefore remains, in a chamber in question, a volume of residual fluid which cannot be driven out and constitutes a damping volume. The vessel may comprise a double wall defining an annular housing for reserve of fluid. The vessel may also be partially made of a porous material such as a ceramic.

The use of a rod 180 of piston 174 traversing the walls of the vessel 172 is advantageous. In effect, this rod 180 and therefore the piston 174 may be connected to the screw 18' while providing that the latter lie outside the vessel 172. This is interesting in terms of tightness, insofar as it is necessary to provide solely one sealing member in the vicinity of the opening of the vessel, through which the afore-mentioned rod extends.

It is also advantageous to provide a device for intervertebral stabilisation, comprising a discal implant and a damping member, disposed to the rear of the intervertebral space. In effect, the intervertebral implant makes it possible to restore the height of the disc. Moreover, being given that this implant contains a fluid, it is adapted to give the two adjacent vertebral bodies a certain mutual freedom of movement. Furthermore, the extra-discal damping member makes it possible to regulate the movements allowed by the discal implant.

Figure 13:
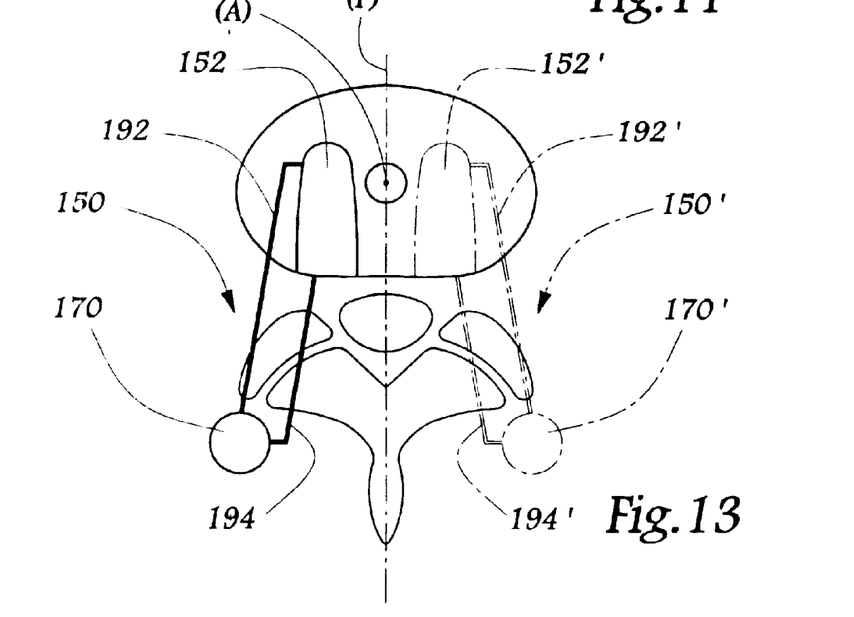
FIG. 13 is a plan view, illustrating an assembly for intervertebral stabilisation according to the invention.

As shown in FIG. 13, the stabilising device 150 may be disposed offset with respect to the principal axis A, namely the implant 152 and the member 170 are disposed on the same side of the plane P. Such an arrangement makes it possible to overcome asymmetrical collapses of the intervertebral space, viewed from behind.

An additional device 150' may be associated with the stabilising device 150, placed on the other side of the axis A and the plane P, so as to form an assembly for intervertebral stabilisation. This device 150' shown in dashed and dotted lines, may be similar to that, 150, it being understood that it is possible to give it different dimensions, in particular concerning the height of the implant 152', so as to compensate a slight asymmetrical collapse of the disc, viewed from behind.

The invention is not limited to the examples described and shown. In effect, it may be provided to connect two vertebrae which are not adjacent, via a device for intervertebral stabilisation according to the invention.

The means for placing in fluid communication described hereinabove control the flow of the fluid as they induce a limitation of the flow of this fluid, during flow thereof between the chambers thus connected. This may be effected by giving these communicating means reduced transverse dimensions, or a considerable length. These means induce a restriction, a slowing down of the fluid and/or a pressure drop of the latter. The flowrate of fluid between the chambers is conserved at a value less than a limiting value, which guarantees that the passage of the fluid from a first chamber towards a second chamber is not too rapid. A certain damping of the movements of the patient's column is thus created.

It is particularly advantageous to provide that two adjacent chambers be separated by a mobile member, such as a piston. In effect, this makes it possible to make extradiscal and/or intradiscal objects which are efficient, take up little room and which are subjected to problems of tightness only to a small degree.

The invention claimed is:

1. An apparatus for engagement relative to two vertebrae of a spine, comprising: a dampening device effective for placement in close proximity to the two vertebrae, the dampening device including a rigid vessel, the vessel including:
   a first inner wall opposite a second inner wall;
   two chambers each extending between the first inner wall and the second inner wall, the chambers each containing a fluid and at least one conduit in fluid communication with each of the chambers to control the flow of the fluid therebetween, the fluid in each of the chambers being in contact with the first inner wall and the second inner wall,
   a mobile separating member extending from the first inner wall to the second inner wall to divide the vessel into the two chambers, the mobile separating member being positioned between the two chambers, and the mobile separating member being in contact with the fluid in each of the two chambers;
   a screw connected to the mobile separating member to move therewith relative to the vessel; and
   wherein the dampening device is responsive to relative motion of the two vertebrae when engaged therewith to selectively change an amount of fluid in one of the chambers relative to an amount of fluid in another of the chambers by passage through the at least one conduit, and to cause motion of the mobile separating member relative to the vessel along the first inner wall and the second inner wall, the mobile separating member being structured to maintain separation of the two chambers during the motion.

2. The apparatus of claim 1, wherein at least one of the chambers includes a wall that is deformable in response to the relative motion.

3. The apparatus of claim 1, wherein the vessel includes a deformable bag connected to a rigid cover to define one of the chambers, the bag and the cover being in contact with the fluid.

4. The apparatus of claim 3, wherein the rigid cover further comprises at least a part of the mobile separating member.

5. The apparatus of claim 1, wherein the chambers are each defined by a respective deformable bag coupled to a respective rigid cover, the respective bag and the respective cover of each of the chambers being in contact with the fluid.

* * * * *